United States Patent [19]

Kuratle, III

[11] 4,121,921
[45] Oct. 24, 1978

[54] METHODS FOR INCREASING RICE CROP YIELDS

[75] Inventor: Henry Kuratle, III, Wilmington, Del.

[73] Assignee: E. I. Du Pont de Nemours and Company, Wilmington, Del.

[21] Appl. No.: 717,284

[22] Filed: Aug. 24, 1976

Related U.S. Application Data

[60] Continuation of Ser. No. 555,998, Mar. 6, 1975, abandoned.
[51] Int. Cl.² .................... A01N 21/02; A01N 9/12; A01N 9/20
[52] U.S. Cl. ........................... 71/77; 71/98; 71/100; 71/111
[58] Field of Search .................. 71/77, 98, 111, 100

[56] References Cited

U.S. PATENT DOCUMENTS

| 3,671,212 | 6/1972 | Jaworski | 71/77 |
| 3,857,879 | 12/1974 | Abramitis | 71/77 |
| 3,901,684 | 8/1975 | Lin | 71/111 |
| 3,933,469 | 1/1976 | Long | 71/98 |
| 3,954,837 | 5/1976 | Bellina | 71/111 |
| 3,959,331 | 5/1976 | Fuchs et al. | 71/98 |

FOREIGN PATENT DOCUMENTS 4,925,133  3/1974  Japan ..................... 71/111

Primary Examiner—Glennon H. Hollrah

[57] ABSTRACT

Methods for increasing the yield of rice crops comprising applying thereto an allophanimidate such as methyl 4-(4-chlorophenyl)-N-methoxycarbonylallophanimidate or methyl 4-(4-chlorophenyl)-N-methylthiocarbonylallophanimidate to the seeds, seedlings, or the soil in which the seeds or seedlings are planted.

20 Claims, No Drawings

METHODS FOR INCREASING RICE CROP YIELDS

This is a continuation of application Ser. No. 555,998, filed Mar. 6, 1975, now abandoned.

BACKGROUND OF THE INVENTION

The allophanimidates used in this invention and their use as herbicides are disclosed and claimed in copending U.S. patent application Ser. No. 325,357, filed Jan. 22, 1973, by Julius J. Fuchs and Kang Lin, which is a continuation-in-part of copending U.S. patent application Ser. No. 181,201, filed Sept. 16, 1971, now abandoned. The use of these compounds in a method for altering plant flowering and sexual reproduction is the subject matter of copending U.S. patent application Ser. No. 328,059, filed Jan. 30, 1973, by Kang Lin, now U.S. Pat. No. 3,901,684. In addition, the use of these compounds in a method for increasing crop yields is disclosed and claimed in copending U.S. patent application Ser. No. 446,800, filed Feb. 28, 1974, by James D. Long, now U.S. Pat. No. 3,933,469 (which is a continuation-in-part of U.S. patent application Ser. No. 414,876, filed Oct. 12, 1973, which is, in turn, a continuation-in-part of U.S. patent application Ser. No. 348,323, filed Apr. 5, 1973, both now abandoned).

In particular, in U.S. Ser. No. 446,800, there is claimed a method for increasing the yield of wheat, rye, and corn crops comprising applying certain allophanimidates to the crop plant during inflorescence initiation or early development.

It has now been discovered that rice crop yields can be significantly increased by applying certain of these allophanimidates to rice seed, to rice seedlings, or to the soil into which these seeds or seedlings have been or will be placed.

SUMMARY OF THE INVENTION

This invention is a method of increasing the yield of rice crops which comprises applying an allophanimidate to rice seeds prior to planting, to rice seedlings prior to, during, or shortly after planting, or to the soil in which rice seeds or seedlings have been planted, are being planted, or will be planted, the allophanimidate being a compound of the formula:

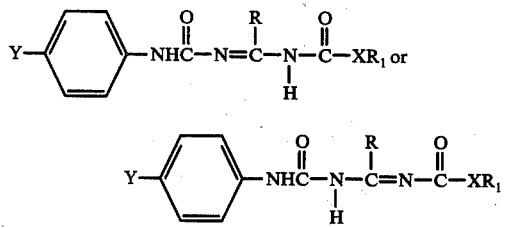

wherein
Y is chlorine, bromine, or iodine;
R is $SR_2$ or $OR_2$;
$R_2$ is methyl or ethyl;
$R_1$ is methyl or ethyl; and
X is oxygen or sulfur.

In particular, this invention is a method for increasing the yield of rice crops which comprises applying an allophanimidate of formula I to rice seeds or seedlings by any one or more of the following mechanisms:

(a) applying the allophanimidate to rice seed by seed soaking prior to planting;

(b) applying the allophanimidate to rice seed by seed treatment, such as seed coating or pelletization, prior to planting;

(c) applying the allophanimidate to rice seedlings by dipping prior to transplanting;

(d) applying the allophanimidate to rice seedlings as a foliar spray at any time from emergence until 80 days after planting; or (e) applying the allophanimidate to rice seeds or seedlings as a soil application or a soil soak treatment, such as during rice field irrigation, shortly before planting, during planting, or at any time thereafter until 80 days after planting.

In addition, this invention comprises the intermediate product produced by the methods (a) and (b) above, i.e., soaked seed and treated (coated or pelletized) seed.

DETAILED DESCRIPTION OF THE INVENTION

Preferred Compounds

Certain of the compounds of Formula I are preferred because of their higher activity and their ease of synthesis. These include compounds of Formula I:
R is $OR_2$;
$R_1$ is methyl;
$R_2$ is methyl; and
X is oxygen.

The most preferred compound because of highest activity is the following:

methyl 4-(4-chlorophenyl)-N-methoxycarbonylallophanimidate

It should be understood that tautomeric forms of the molecule are possible

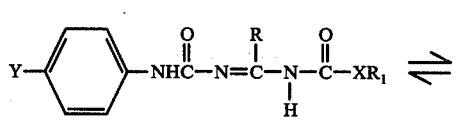

Form (A)

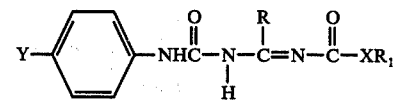

Form (B)

For this reason, all compounds used in the present invention are named allophanimidates according to form (A).

SYNTHESIS OF THE COMPOUNDS

The compounds of Formula I can be made by the process illustrated by the following equations:

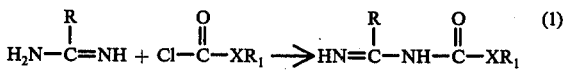

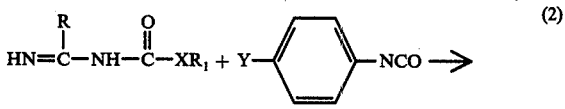

-continued

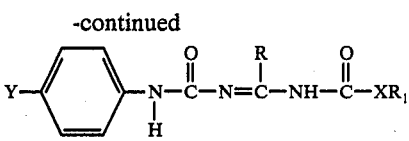

where R and $R_1$ are as previously defined.

The allophanimidates of Formula I can be obtained by reacting the pseudourea or thiopseudourea first with a chloroformate or thiolchloroformate as in equation (1), and then reacting the reaction products of equation (1) with an isocyanate [as in equation (2)]. (See, e.g., U.S. Pat. No. 3,855,219, granted Dec. 17, 1974, to Julius J. Fuchs and Kang Lin, pertinent subject matter of which is hereby incorporated by reference.)

The following examples are offered to illustrate the processes described above. All parts are parts by weight unless otherwise indicated.

EXAMPLE 1

Methyl 4-(4-chlorophenyl)-N-methoxycarbonylallophanimidate

To 52 parts of 2-methylpseudourea hydrogen sulfate in 250 parts of water at 0°–5° C. is added 31 parts of methyl chloroformate followed by dropwise addition of 74 parts of 50% sodium hydroxide. The reaction mass is stirred at room temperature for 3 hours and then extracted with methylene chloride. The methylene chloride extract is dried and the solvent evaporated. The residue is triturated with hexane to give 23 parts of methyl N-(1-amino-1-methoxy methylene)carbamate melting at 36°–39.5° C.

To 13 parts of this methyl N-(1-amino-1-methoxymethylene)carbamate, m.p. 36°–39.5° in 140 parts of methylene chloride is added 15 parts of 4-chlorophenyl isocyanate. The reaction mixture is stirred overnight and the solution filtered to give 10 parts of methyl 4-(4-chlorophenyl)-N-methoxycarbonylallophanimidate melting at 170° dec.

EXAMPLE 2

Methyl 4-(4-chlorophenyl)-N-methylthiolcarbonylallophanimidate

To 9 parts of methyl N-(1-amino-1-methoxymethylene)thiolcarbamate, m.p. 55°–57° (prepared similar to the procedure in Example 1 for methyl N-(1-amino-1-methoxymethylene)carbamate in 20 parts of methylene chloride is added 9 parts of 4-chlorophenyl isocyanate. The reaction mixture is stirred overnight and the solution is filtered to give 14 parts of methyl 4-(4-chlorophenyl)-N-methylthiolcarbonylallophanimidate melting at 153°–155°.

The following allophanimidates can be prepared by the procedure of Example 1 by substituting the listed 2-substituted thiopseudoureas and pseudoureas for 2-methyl pseudourea, by replacing 4-chlorophenyl isocyanate with various isocyanates and by using various chloroformates or chlorothiolformates in place of methyl chloroformate.

| Pseudourea or Pseudothiourea | Isocyanate | Formate or Thiolformate | Allophanimidate |
|---|---|---|---|
| 2-methyl pseudourea | 4-chlorophenyl isocyanate | methyl chloroformate | methyl 4-(4-chlorophenyl)-N-methoxycarbonylallophanimidate |
| 2-methyl pseudourea | 4-chlorophenyl isocyanate | methyl chlorothiolformate | methyl 4-methyl 4-(4-chlorophenyl)-N-methylthiolcarbonylallophanimidate |
| 2-ethyl pseudourea | 4-chlorophenyl isocyanate | methyl pseudourea | ethyl 4-(4-chlorophenyl)-N-methoxycarbonylallophanimidate |
| 2-ethyl pseudourea | 4-chlorophenyl isocyanate | methyl chlorothiolformate | ethyl 4-(4-chlorophenyl)-N-methylthiolcarbonylallophanimidate |
| 2-methyl pseudourea | 4-chlorophenyl isocyanate | kpseudourea | methyl 4-(4-chlorophenyl)-N-ethoxycarbonylallophanimidate |
| 2-methyl pseudourea | 4-chlorophenyl isocyanate | ethyl chlorothiolformate | methyl 4-(4-chlorophenyl)-N-ethylthiolcarbonylallophanimidate |
| 2-ethyl pseudourea | 4-chlorophenyl isocyanate | kpseudourea | ethyl 4-(4-chlorophenyl)-N-ethoxycarbonylallophanimidate |
| 2-ethyl pseudourea | 4-chlorophenyl isocyanate | ethyl chlorothiolformate | ethyl 4-(4-chlorophenyl)-N-ethylthiolcarbonylallophanimidate |
| 2-methyl-2-thiopseudourea | 4-chlorophenyl isocyanate | methyl chloroformate | methyl 4-(4-chlorophenyl)-N-methoxycarbonylthioallophanimidate |
| 2-methyl-2-thiopseudourea | 4-chlorophenyl isocyanate | methyl chlorothiolformate | methyl 4-(4-chlorophenyl)-N-methylthiolcarbonylthioallophanimidate |
| 2-ethyl-2-thiopseudourea | 4-chlorophenyl isocyanate | methyl chloroformate | esthyl 4-(4-chlorophenyl)-N-methoxycarbonylthioallophanimidate |
| 2-ethyl-2-thiopseudourea | 4-chlorophenyl isocyanate | methyl chlorothiolformate | ethyl 4-(4-chlorophenyl)-N-methylthiolcarbonylthioallophanimidate |
| 2-methyl-2-thiopseudourea | 4-chlorophenyl isocyanate | ethyl chloroformate | methyl 4-(4-chlorophenyl)-N-ethoxycarbonylthioallophanimidate |
| 2-methyl-2-thiopseudourea | 4-chlorophenyl isocyanate | ethyl chlorothiolformate | methyl 4-(4-chlorophenyl)-N-ethylthiolcarbonylthioallophanimidate |
| 2-ethyl-2-thiopseudourea | 4-chlorophenyl isocyanate | ethyl chloroformate | ethyl 4-(4-chlorophenyl)-N-ethoxycarbonylthioallophanimidate |
| 2-ethyl-2-thiopseudourea | 4-chlorophenyl isocyanate | ethyl chlorothiolformate | ethyl 4-(4-chlorophenyl)-N-ethylthiolcarbonylthioallophanimidate |
| 2-methyl pseudourea | 4-bromophenyl isocyanate | methyl chloroformate | methyl 4-(4-bromophenyl)-N-methoxycarbonylallophanimidate |
| 2-methyl pseudourea | 4-bromophenyl isocyanate | methyl chlorothiolformate | methyl 4-(4-bromophenyl)-N-methylthiolcarbonylallophanimidate |
| 2-ethyl pseudourea | 4-bromophenyl isocyanate | methyl chloroformate | ethyl 4-(4-bromophenyl)-N-methoxycarbonylallophanimidate |
| 2-ethyl pseudourea | 4-bromophenyl isocyanate | methyl chlorothiolformate | ethyl 4-(4-bromophenyl)-N-methylthiolcarbonylallophanimidate |
| 2-methyl pseudourea | 4-bromophenyl isocyanate | ethyl chloroformate | methyl 4-(4-bromophenyl)-N-ethoxycarbonylallophanimidate |
| 2-methyl pseudourea | 4-bromophenyl isocyanate | ethyl chlorothiolformate | methyl 4-(4-bromophenyl)-N-ethylthiolcarbonylallophanimidate |

-continued

| Pseudourea or Pseudothiourea | Isocyanate | Formate or Thiolformate | Allophanimidate |
|---|---|---|---|
| 2-ethyl pseudourea | 4-bromophenyl isocyanate | ethyl chloroformate | ethyl 4-(4-bromophenyl)-N-ethoxy-carbonylallophanimidate |
| 2-ethyl pseudourea | 4-bromophenyl isocyanate | ethyl chlorothiolformate | ethyl 4-(4-bromophenyl)-N-ethyl-thiolcarbonylallophanimidate |
| 2-methyl-2-thio-pseudourea | 4-bromophenyl isocyanate | methyl chloroformate | methyl 4-(4-bromophenyl)-N-methoxy-carbonylthioallophanimidate |
| 2-methyl-2-thio-pseudourea | 4-bromophenyl isocyanate | methyl chlorothiolformate | methyl 4-(4-bromophenyl)-N-methyl-thiolcarbonylthioallophanimidate |
| 2-ethyl-2-thio-pseudourea | 4-bromophenyl isocyanate | methyl chloroformate | ethyl 4-(4-bromophenyl)-N-methoxy-carbonylthioallophanimidate |
| 2-ethyl-2-thio-bx | 4-bromophenyl isocyanate | methyl chlorothiolformate | ethyl 4-(4-bromophenyl)-N-methyl-thiolcarbonylthioallophanimidate |
| 2-methyl-2-thio-pseudourea | 4-bromophenyl isocyanate | ethyl chloroformate | methyl 4-(4-bromophenyl)-N-ethoxy-carbonylthioallophanimidate |
| 2-methyl-2-thio-pseudourea | 4-bromophenyl isocyanate | ethyl chlorothiolformate | methyl 4-(4-bromophenyl)-N-ethyl-thiolcarbonylthioallophanimidate |
| 2-ethyl-2-thio-pseudourea | 4-bromophenyl isocyanate | ethyl chloroformate | ethyl 4-(4-bromophenyl)-N-ethoxy-carbonylthioallophanimidate |
| 2-ethyl-2-thio-pseudourea | 4-bromophenyl isocyanate | ethyl chlorothiolformate | ethyl 4-(4-bromophenyl)-N-ethylthiolcarbonylthioallophanimidate |
| 2-methyl pseudourea | 4-iodophenyl isocyanate | methyl chloroformate | methyl 4-(4-iodophenyl)-N-methoxy-carbonylallophanimidate |
| 2-methyl pseudourea | 4-iodophenyl isocyanate | methyl chlorothiolformate | methyl 4-(4-iodophenyl)-N-methyl-thiolcarbonylallophanimidate |
| 2-ethyl pseudourea | 4-iodophenyl isocyanate | methyl chloroformate | ethyl 4-(4-iodophenyl)-N-methoxy-carbonylallophanimidate |
| 2-ethyl pseudourea | 4-iodophenyl isocyanate | methyl chlorothiolformate | ethyl 4-(4-iodophenyl)-N-methyl-thiolcarbonylallophanimidate |
| 2-methyl pseudourea | 4-iodophenyl isocyanate | ethyl chloroformate | methyl 4-(4-iodophenyl)-N-ethoxy-carbonylallophanimidate |
| 2-methyl pseudourea | 4-iodophenyl isocyanate | ethyl chlorothiolformate | methyl 4-(4-iodophenyl)-N-ethyl-thiolcarbonylallophanimidate |
| 2-ethyl pseudourea | 4-iodophenyl isocyanate | ethyl chloroformate | ethyl 4-(4-iodophenyl)-N-ethoxy-carbonylallophanimidate |
| 2-ethyl pseudourea | 4-iodophenyl isocyanate | ethyl chlorothiolformate | ethyl 4-(4-iodophenyl)-N-ethyl-thiolcarbonylallophanimidate |
| 2-methyl-2-thio-pseudourea | 4-iodophenyl isocyanate | methyl chloroformate | methyl 4-(4-iodophenyl)-N-methoxy-carbonylthioallophanimidate |
| 2-methyl-2-thio-pseudourea | 4-iodophenyl isocyanate | methyl chlorothiolformate | methyl 4-(4-iodophenyl)-N-methyl-thiolcarbonylthioallophanimidate |
| 2-ethyl-2-thio-pseudourea | 4-iodophenyl isocyanate | methyl chloroformate | ethyl 4-(4-iodophenyl)-N-methoxy-carbonylthioallophanimidate |
| 2-ethyl-2-thio-pseudourea | 4-iodophenyl isocyanate | methyl chlorothiolformate | ethyl 4-(4-iodophenyl)-N-methyl-thiolcarbonylthioallophanimidate |
| 2-methyl-2-thio-pseudourea | 4-iodophenyl isocyanate | ethyl chloroformate | methyl 4-(4-iodophenyl)-N-ethoxy-carbonylthioallophanimidate |
| 2-methyl-2-thio-pseudourea | 4-iodophenyl isocyanate | ethyl chlorothiolformate | methyl 4-(4-iodophenyl)-N-ethyl-thiolcarbonylthioallophanimidate |
| 2-ethyl-2-thio-pseudourea | 4-iodophenyl isocyanate | ethyl chloroformate | ethyl 4-(4-iodophenyl)-N-ethoxy-carbonylthioallophanimidate |
| 2-ethyl-2-thio-pseudourea | 4-iodophenyl isocyanate | ethyl chlorothiolformate | ethyl 4-(4-iodophenyl)-N-ethyl-thiolcarbonylthioallophanimidate |

USE OF THE COMPOUNDS

The compounds of formula I can be used to increase the yield of rice, one of the most important food crops of the world. Treatment of the rice seed or the young plants (via soil application of foliar spray) results in more grain produced per unit area. The rate of treatment will vary depending on the compound, method of application, time of application, and soil type (soil application).

In the case of seed soaking, soaking duration can range from ¼ to 24 hours. A soaking period of ½ to 12 hours is preferred, with 1–6 hours being most preferred. The aqueous seed soaking solution should contain 1,000–15,000 p.p.m. of a compound of formula I; 4,000–10,000 p.p.m. is preferred.

In the case of seed treatment, the compound can be applied as a solid seed coating, thus creating pelleted seed, or as a dust on the surface of the seed. The seeds are treated with 30–3,000 grams of a compound of formula I per 100 kg of seed; 60–1,250 grams per 100 kg of seed is preferred with 125–500 grams per 100 kg of seed most preferred.

In the case of transplant dipping the concentration of the compounds of formula I in the dip solution can be 1,000–15,000 ppm with 4,000–10,000 ppm preferred. Dipping time can be ¼ to 24 hours; a dipping time of ½ to 12 hours is preferred with 1–6 hours most preferred.

Finally, in the case of both foliar spray and soil application, the compounds of formula I are applied to the rice foliage or to the soil in which the rice is planted at application rates from ¼ to 6 kg/ha; ½ to 4 kg/ha is preferred, and 1–3 kg/ha is most preferred. Application time may range from planting, or shortly before, to 80 days thereafter. It is preferred to apply the compound prior to 65 days after planting with the most preferred time of application being 10–45 days after planting.

Formulation of the Compounds

Useful formulations of the compounds of formula I can be prepared in conventional ways. They include dusts, granules, pellets, solutions, suspensions, emulsions, wettable powders, emulsifiable concentrates, and the like. Many of these may be applied directly. Sprayable formulations can be extended in suitable media and used at spray volumes of from a few pints to several hundred gallons per acre. High strength compositions are primarily used as intermediates for further formulation. Many of the formulations can be applied as seed coatings or extended in a suitable media or used as dip solutions. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20-90 | 0-74 | 1-10 |
| Oil Suspensions, Emulsions, Solutions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd, Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Coloring agents can also be added. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th. Edn., McGraw-Hill, New York, 1963, pp. 8–59ff.

For further information regarding the art of formulation, see, for example:

H. M. Loux, U.S. Pat. No. 3,235,361 Feb. 15, 1966, Col. 6, Line 16 through Col. 7, Line 19, and Examples 10 through 41.

R. W. Luckenbaugh, U.S. Pat. No. 3,309,192, Mar. 14, 1967, Col. 5, Line 43 through Col. 7, Line 62, and Examples 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, Line 66 through Col. 5, Line 17, and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Edn. Blackwell Scientific Publications, Oxford, 1968, pp. 101–103.

Examples of suitable formulations of compounds used in the method of the present invention include the following:

EXAMPLE 3

| Wettable Powder | |
| --- | --- |
| methyl 4-(4-chlorophenyl)-N-methoxy-carbonylallophanimidate | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S. Ser. No. 50 sieve (0.3 mm opening) before packaging.

All compounds used in this invention may be formulated in the same manner.

EXAMPLE 4

| High Strength Concentrate | |
| --- | --- |
| methy 4-(4-chlorophenyl)-N-methyl-thiolcarbonylallophanimidate | 98.5% |
| silical aerogel | 0.5% |
| synthetic amorphous fine silica | 1.0% |

Blend and grind the ingredients in a hammer mill to produce a high strength concentrate essentially all passing a U.S. Ser. No. 50 sieve (0.3 mm openings). This material may then be formulated in a variety of ways.

EXAMPLE 5

| Dust | |
| --- | --- |
| high strength concentrate, Example (above) | 25.4% |
| pyrophyllite, powdered | 74.6% |

The materials are thoroughly blended and packaged for use.

EXAMPLE 6

| Aqueous Suspension | |
| --- | --- |
| methyl 4-(4-chlorophenyl)-N-methoxy-carbonylallophanimidate | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 7

| Oil Suspension | |
| --- | --- |
| methyl 4-(4-chlorophenyl)-N-methoxy-carbonyl-1-thioallophanimidate | 25% |
| polyoxyethylene sorbitol hexaoleate | 5% |
| highly aliphatic hydrocarbon oil | 70% |

9

Grind the ingredients together in a sand mill until the solid particles have been reduced to under about 5 microns. The resulting thick suspension may be applied directly, but preferably after being extended with oils or emulsified in water.

EXAMPLE 8

| Solution | |
|---|---|
| methyl 4-(4-chlorophenyl)-N-methoxy-carbonyl-1-thioallophanimidate | 25% |
| dimethylformamide | 75% |

The ingredients are combined and stirred to produce a solution. This can be used for low volume application.

EXAMPLE 9

Granules

The solution of Example 8 (above) is sprayed onto preformed montmorillonoid clay granules (0.6–2.5 mm in diameter) tumbling in a rotating drum. The rate of spray is adjusted to produce a 5% active granule. These are then packaged and are ready for use.

EXAMPLE 10

| Seed Treatment Wettable Powder | |
|---|---|
| methyl 4-(4-chlorophenyl)-N-methoxy-carbonylallophanimidate | 60.0% |
| Polyfon® H (Sugar-free, sodium-based sulfonates of Kraft lignin) | 4.0% |
| Tergitol® TMN (Trimethyl nonyl polyethylene glycol ether) diaxomaceous earth | 4.0% 27.0% |
| Rhodamine B extra (dye) | 1.0% |
| Sugar | 4.0% |

The liquid Tergitol ® is thoroughly mixed with the diatomaceous earth to produce a uniform, dry mixture. The remaining ingredients are then added, blended, and ground in a hammer mill to produce a powder essentially all passing a U.S. Ser. No. 50 sieve (0.3 mm openings).

Seeds are coated using an aqueous slurry of this formulation.

EXAMPLE 11

| Seed Pelleting Formulation | |
|---|---|
| methyl 4-(4-chlorophenyl)-N-methyl-thiolcarbonylallophanimidate | 1.0% |
| Polyfon® H (Sugar-free, sodium-based sulfonates of Kraft lignin) | 0.5% |
| Kaolinite clay | 98.5% |

The ingredients are thoroughly blended and ground through a hammer mill to produce a powder essentially all passing a U.S. Ser. No. 50 sieve (0.3 mm. opening).

Seeds and an appropriate amount of the above formulation, to yield from 30 g to 3,000 g of active per kg of seeds, are placed on a rotating pan granulator. As the seeds and formulation are tumbled on the granulator, enough water is sprayed onto the mixture to cause the powder to adhere to the seeds. The seeds are dried and are ready for use.

What is claimed is:

1. A method for increasing the yield of rice crops which comprises applying an effective amount of an allophanimidate to rice seeds, seedlings, or to soil in which rice seeds or seedlings are planted, not later than 65 days after planting, the allophanimidate being a compound of the formula

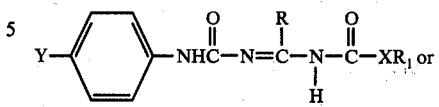

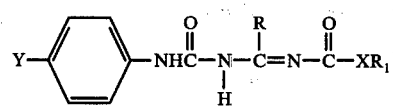

wherein
Y is chlorine, bromine or iodine;
R is $SR_2$ or $OR_2$;
$R_2$ is methyl or ethyl;
$R_1$ is methyl or ethyl; and
X is oxygen or sulfur.

2. Method of claim 1 wherein the allophanimidate is selected from the group consisting of compounds of formula I wherein
Y is chlorine, bromine, or iodine;
R is $OR_2$;
$R_1$ is methyl;
$R_2$ is methyl; and
X is oxygen.

3. Method of claim 1 wherein the allophanimidate is methyl 4-(4-chlorophenyl)-N-methoxycarbonylallophanimidate.

4. Method of claim 1 wherein the allophanimidate is applied to the seed by seed soaking prior to seed planting.

5. Method of claim 4 wherein the allophanimidate is applied to the seed by soaking for ¼ to 24 hours in a solution containing 1,000 to 15,000 ppm of the allophanimidate.

6. Method of claim 4 wherein the allophanimidate is applied to the seed by soaking ½ to 12 hours in a solution containing 4,000 to 10,000 ppm of the allophanimidate.

7. Method of claim 4 wherein the allophanimidate is applied to the seed by soaking 1 to 6 hours in a solution containing 4,000 to 10,000 ppm of the allophanimidate.

8. Method of claim 1 wherein the allophanimidate is applied to the seed by seed treatment prior to planting.

9. Method of claim 8 wherein the seed treatment is selected from the group consisting of seed coating and seed pelletization.

10. Method of claim 9 wherein the seeds are treated with 30 to 30,000 grams of allophanimidate per 100 kg of seed.

11. Method of claim 9 wherein the seed is treated with 60 to 1,250 grams of allophanimidate per 100 kg of seed.

12. Method of claim 9 wherein the seed is treated with 125 to 500 grams of allophanimidate per 100 kg of seed.

13. Method of claim 1 wherein the allophanimidate is applied to the rice seedlings by dipping prior to transplanting.

14. Method of claim 13 wherein the allophanimidate is applied to the rice seedlings by dipping for ¼ to 24 hours in a solution containing 1,000 to 15,000 ppm of the allophanimidate.

15. Method of claim 13 wherein the allophanimidate is applied to the rice seedlings by dipping for ½ to 12 hours in a solution containing 4,000 to 10,000 ppm of the allophanimidate.

16. Method of claim 13 wherein the allophanimidate is applied to the rice seedlings by dipping for 1 to 6 hours in a solution containing 4,000 to 10,000 ppm of the allophanimidate.

17. Method of claim 1 wherein the allophanimidate is applied to the seeds or seedlings by a technique selected from the group consisting of foliar spray and soil application.

18. Method of claim 17 wherein the allophanimidate is applied to the planted seeds or seedlings at a rate of ¼ to 6 kg/Ha.

19. Method of claim 17 wherein the allophanimidate is applied to the planted seeds or seedlings and at a rate of ½ to 4 kg/Ha.

20. Method of claim 17 wherein the allophanimidate is applied to the planted seeds or seedlings between 10 and 45 days after planting and at a rate of 1 to 3 kg/Ha.

* * * * *